United States Patent
Espada Regalado et al.

(10) Patent No.: US 10,695,428 B2
(45) Date of Patent: Jun. 30, 2020

(54) USE OF A PHOTOSENSITIVE AGENT CAPABLE OF PRODUCING REACTIVE OXYGEN SPECIES IN THE PRODUCTION OF A DRUG FOR THE PHOTODYNAMIC THERAPY OF A DISEASE RELATED TO STEM CELLS, IN VITRO USE, AND PHARMACEUTICAL COMPOSITION

(71) Applicants: UNIVERSIDAD AUTONOMA DE MADRID, Madrid (ES); CONSEJO SUPERIOR DE INVESTIGACIONES CIENTIFICAS, Madrid (ES)

(72) Inventors: Jesus Espada Regalado, Madrid (ES); Elisa Carrasco Cerro, Madrid (ES); María Inmaculada Calvo Sanchez, Madrid (ES); Alfonso Blazquez-Castro, Madrid (ES); Angeles Juarranz De La Fuente, Madrid (ES)

(73) Assignees: UNIVERSIDAD AUTONOMA DE MADRID, Madrid (ES); CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 0 days.

(21) Appl. No.: 14/442,876

(22) PCT Filed: Nov. 11, 2013

(86) PCT No.: PCT/ES2013/070779
§ 371 (c)(1),
(2) Date: May 14, 2015

(87) PCT Pub. No.: WO2014/076338
PCT Pub. Date: May 22, 2014

(65) Prior Publication Data
US 2015/0335746 A1 Nov. 26, 2015

(30) Foreign Application Priority Data

Nov. 14, 2012 (ES) .................................. 201231759

(51) Int. Cl.
*A61K 41/00* (2020.01)
*A61K 8/49* (2006.01)
*A61K 31/409* (2006.01)
*A61K 8/44* (2006.01)
*A61Q 19/00* (2006.01)

(52) U.S. Cl.
CPC ............ *A61K 41/0071* (2013.01); *A61K 8/44* (2013.01); *A61K 8/492* (2013.01); *A61K 8/494* (2013.01); *A61K 31/409* (2013.01); *A61K 41/0061* (2013.01); *A61Q 19/00* (2013.01); *A61K 2800/10* (2013.01)

(58) Field of Classification Search
None
See application file for complete search history.

(56) References Cited

U.S. PATENT DOCUMENTS

2007/0225518 A1* 9/2007 Malik .................. A61K 8/44
562/8
2010/0222538 A1 9/2010 Kwon et al.

FOREIGN PATENT DOCUMENTS

WO 2010015087 A1 2/2010
WO 2012040105 A2 3/2012

OTHER PUBLICATIONS

Ortel et al. British Journal of Cancer 1998 77(11):1744-1751.*
Roh et al. Journal of Investigative Dermatology 2005 125:1099-1105.*
Blazquez-Castro et al.European Journal of Cell Biology 2012 91:216-223.*
Espada et al. Journal of Cell Biology 2008 181(1):27-35.*
Blanpain et al. Annual Review of Cell and Developmental Biology 2006 22:339-373.*
Häkkinen et al. Methods of Cell Science 2002 23:189-196.*
Hennings Cell 1980 19(1):245-254.*
Hermes-Lima Free Radical Biology and Medicine 1995 19(3):381-390.*
Janes et al. Journal of Pathology 2002 197:479-491.*
Chiu et al. Lasers in Surgery and Medicine 2005 37:231-244 (Year: 2005).*
Kolodka et al. Proceedings of the National Academy of Sciences 1998 95:4356-4361 (Year: 1998).*
Guo et al. Isolation and Culture of Adult Epithelial Stem Cells from Human Skin. Journal of Visual Experiments 49. www.jove.com/details.php?id=2561 pp. 1-4 (Year: 2011).*
Winkler et al. European Journal ofPharmaceutics and Biopharmaceutics 2002 53:281-287 (Year: 2002).*
International Search Report dated Feb. 14, 2014 for PCT/ES2013/070779 and English translation.
Jose L. Sardina, et al; Reactive oxygen species: Are they important for haematopoiesis?; Critical Reviews in Oncology/Hematology; vol. 81; 2012; pp. 257-274.
Li Zhang, et al; An updated view on stem cell differentiation into smooth muscle cells; Vascular Pharmacology; vol. 56; 2012; pp. 280-287.

(Continued)

*Primary Examiner* — Robert A Wax
*Assistant Examiner* — Caralynne E Helm
(74) *Attorney, Agent, or Firm* — Squire Patton Boggs (US) LLP

(57) ABSTRACT

The invention relates to the use of a photosensitive agent, or the precursor thereof, capable of producing reactive oxygen species (ROS) in the production of a drug that can be used for the photodynamic therapy (PDT)-based treatment of a disease related to a patient's stem cells, preferably epidermal stem cells.

3 Claims, 6 Drawing Sheets

(56) References Cited

OTHER PUBLICATIONS

Ar-Ri Ji, et al; Reactive oxygen species enhance differentiation of human embryonic stem cells into mesendodermal lineage; Experimental and Molecular Medicine; vol. 42; No. 3; Mar. 2010; pp. 175-186.

Jaggi Rao, et al; Photodynamic therapy for the dermatologist; Medscape Reference; 14 pages.

* cited by examiner

USE OF A PHOTOSENSITIVE AGENT CAPABLE OF PRODUCING REACTIVE OXYGEN SPECIES IN THE PRODUCTION OF A DRUG FOR THE PHOTODYNAMIC THERAPY OF A DISEASE RELATED TO STEM CELLS, IN VITRO USE, AND PHARMACEUTICAL COMPOSITION

CROSS REFERENCE TO RELATED APPLICATION

This Application is a 371 of PCT/ES2013/070779 filed on Nov. 11, 2013 which, in turn, claimed the priority of Spanish Patent Application No. P201231759 filed on Nov. 14, 2012, both applications are incorporated herein by reference.

FIELD OF THE INVENTION

The present invention relates to a second medical indication of Reactive Oxygen Species (ROS) in the medical field of the diseases related to stem cells in a subject.

BACKGROUND

The Photodynamic Therapy (PDT) is a therapeutic modality of clinical use widely used for the treatment of various skin diseases, including cancer.

PDT is based on the exogenous administration of photosensitive compounds (PS) or precursors of the same which accumulate by means of different mechanisms in a preferred manner in the target tissues. The irradiation of the tissue with light of appropriate wavelength, usually in the red region of the spectrum ($\lambda \geq 600$ nm) for greater penetration into the tissue, and in the presence of intracellular oxygen induces the production of Reactive Oxygen Species (ROS), especially singlet oxygen. The rapid accumulation of intracellular ROS above a critical threshold promotes a strong photosensitization inducing cell death.

The 5-aminolevulinic acid (ALA) and, to a greater extent, its methylated derivative methyl aminolevulinate (MAL), are two of the most used compounds in a clinical setting, in dermatological protocols with PDT. Their low molecular weight determines a high absorption through the epidermis allowing topical application of the same. These compounds are not photoactive by themselves, but act as precursors of the endogenous PS protoporphyrin IX (PpIX). Once absorbed by the cell, they are incorporated in the metabolic pathway of the biosynthesis of heme group promoting an abnormal accumulation of PpIX that can last between hours and days, with the subsequent photosensitization of the target tissue. The MAL-PDT treatment is widespread in clinical dermatology, particularly for the treatment of actinic keratosis and basal cell carcinoma.

It has been described that the experimental treatment with exogenous sources of ROS in low amounts, such as hydrogen peroxide, can promote cell proliferation in in vitro cultures (Boonstra J, Post J A. "Molecular events associated with reactive oxygen species and cell cycle progression in mammalian cells". Gene 337: 1-13, 2004), including potential neural progenitor cells grown by the system of neurospheres (Le Belle J E et al. "Proliferative neural stem cells have high endogenous ROS levels that regulate self-renewal and neurogenesis in a PI3K/Akt- dependant manner", Cell Stem Cell. 8: 59-71, 2011).

However, there is so far no experimental evidence to suggest a causal relationship between endogenous production of ROS in a tissue and the functional activation of a type of stem cell contained in said tissue involving physiological consequences, with potential clinical, pharmacologic or cosmetic use. This is largely because there is no in vivo experimental procedure that allows inducing a controlled endogenous production of ROS in a tissue.

There are also no experimental data indicating that endogenous ROS accumulation in tissues can be part of a normal homeostatic process functionally dependent on stem cells. On the contrary, all the experimental results showing an in vivo accumulation of ROS in tissues indicate that this accumulation is abnormal and is associated with pathologic conditions and aging processes (Valko M et al. "Free radicals and antioxidants in normal physiological functions and human disease", Int. J. Biochem. Cell Biol. 39: 44-84, 2007). Also, the topical treatment of a tissue with exogenous sources of ROS can not be considered in any way biologically equivalent to a physiological production of endogenous ROS.

The inventors describe an experimental method that uses PDT-MAL to induce endogenous production of ROS in the hair follicle capable of activating the epidermal stem cells contained in this niche. This stimulation of the epidermal stem cells is due to the transcriptional activation by ROS in the target tissue of the genes of the prolactin family 2, also known as proliferins, particularly proliferin-2 or Prl2c3. Taking into account that there has been proposed a potential role for Prl2c3 in the in vitro expansion of hematopoietic stem cells (Choong M L et al. "A novel role for proliferin-2 in the ex vivo expansion of hematopoietic stem cells", FEBS Lett. 550: 155-62, 2003), the in vivo stimulation of genes of the proliferin family by ROS associated with an activation of epidermal stem cells is a surprising and important discovery in its own right.

In the current art, one of the most widespread uses of the epidermal stem cells in the field of bioengineering is the generation of skin equivalents of epidermal or dermo-epidermal component (Shevchenko R V et al. "A review of tissue-engineered skin bioconstructs available for skin reconstruction", J. R. Soc. Interface 7: 229-58, 2010). These skin equivalents or artificial skins have very important applications in regenerative medicine, primarily for the treatment of burns and wounds of great extent and depth. The ideal treatment for this type of injury is the autograft with different types of skin equivalents generated from skin of the own patient. Given the restrictions in the European Union (Directive 2010/63/EU) and other countries for the use of experimental animals, another key application of skin equivalents is their use as biological models to test the feasibility and toxicity of pharmaceutical and cosmetic compounds.

In this type of applications an essential limitation is the generation time of a functional skin equivalent, which requires the ex vivo expansion of the epidermal progenitors and the stratification of the epidermal component in contact with air. In a clinical setting, the excessively long time in the production of equivalents for autograft pose an immediate danger to the patient, which requires the use of alternative therapies such as cadaver skin grafts or little humanized synthetic equivalents. In pharmacology and cosmetics, the generation time of artificial skin is directly related to its production cost. Therefore, a problem that arises in the art is to develop an experimental method to speed up these processes during the formation of the skin equivalent.

On the other side, different experimental evidence indicates that many skin diseases, including different types of cancer, alopecia and processes such as aging may be due to a defect in the activity of epidermal stem cells, and in particular of those residing in the niche of the hair follicle. A major limitation in the clinical management of these diseases is that the treatments currently available are symptomatic and nonspecific, that is, they are not intended to functionally modulate the activity of the epidermal stem cells.

The problem that arises in the art, therefore, is to develop methods more specific and effective than the current methods to generate the skin equivalents and treat diseases related to stem cells. The solution provided by the present invention is a treatment by means of a PDT method capable of inducing the endogenous production of ROS and the activation of epidermal stem cells.

DESCRIPTION

The present invention is the use of a photosensitive agent, or the precursor thereof, capable of producing reactive oxygen species in the production of a drug useful for the photodynamic therapy-based treatment of a disease related to stem cells in a subject, preferably epidermal stem cells. In another embodiment of the invention said stem cells are hematopoietic stem cells.

In the present application "photosensitive agent" means a compound capable of producing ROS in the presence of oxygen when irradiated with light of a suitable wavelength, which is administered exogenously or produced by the body itself from a precursor.

In the present application "precursor of a photosensitive agent" means a compound administered by exogenous route from which a photosensitive compound is produced in the cell.

In the present application "Reactive Oxygen Species" or ROS means the compounds having ions and radicals free of oxygen and peroxides.

In the present application "Photodynamic Therapy" or PDT means a method by means of which the production of ROS in a target tissue is induced after promoting the accumulation in said tissue of a photosensitive agent and irradiating it in the presence of oxygen with light of a suitable wavelength.

In the present application "diseases related to stem cells" means those diseases that are accompanied by malfunctions in the homeostatic maintenance of the tissues and that, consequently, directly involve a loss or functional deregulation of the activity of said stem cells (Wagers, A J. "The stem cell niche in regenerative medicine". Cell Stem Cell, 10: 362-369, 2012).

In a preferred embodiment of the invention, said photosensitive agent is protoporphyrin IX (PpIX). In another preferred embodiment said precursor of a photosensitive agent is a precursor of PpIX, still more preferably 5-aminolevulinic acid or the chemical derivatives thereof, and among these chemical derivatives the most preferred is methyl aminolevulinate (MAL).

In the present application "chemical derivative" of the 5-aminolevulinic acid (ALA) means an organic compound containing the basic chemical structure of ALA having one or more chemical substituents or radicals on any of the atoms of said basic structure.

Another preferred embodiment of the use of the invention is that said subject on which the photodynamic therapy is applied is a mammal, preferably human.

The invention describes a PDT adapted methodology that allows generating a controlled and endogenous production of ROS specifically in the prominent region of the hair follicle. Consequently, an activation of the proliferation of the epidermal stem cells contained in this niche, an acceleration of the growth of the hair, an increase of collagen in the dermis and the induction of the expression of the genes of the prolactin family 2 (proliferins), particularly Prl2c3, occur.

The epidermal stem cells are responsible for the homeostatic maintenance of the skin, and their activity is related to all the skin diseases that affect the homeostasis of the skin, cancerous or not, as well as the processes related to aging such as wrinkles or hair loss and to the healing of wounds and burns.

Thus, another additional preferred embodiment is that said disease related to stem cells is a dermatosis or skin disease, more preferably cancer and still more preferably a basal cell carcinoma, squamous cell carcinoma, Bowen's disease, extramammary Paget's disease, melanoma or Gorlin syndrome; or collagen diseases, adermatoglyphia, acrochordon, a hair follicle disease preferably alopecia, Bloom syndrome, atopic dermatitis, discolorations, hairy dysplasia, epidermolysis bullosa, stretch marks, photoallergy, hemangiomas, hyperpigmentation, ichthyosis, follicular mucinosis, necrobiosis lipoidica, nevus, psoriasis, keratosis, seborrhea, Graham-Little syndrome, loose anagen hair syndrome, vitiligo, xerosis or degenerative processes associated with normal or pathological aging.

In another additional preferred embodiment said drug is administered topically.

Another preferred embodiment of the invention is the use of a photosensitive agent, or the precursor thereof, capable of producing ROS, and at least another therapeutic agent in the production of a drug useful for the treatment by PDT of a disease related to stem cells in a subject, preferably epidermal.

Another additional preferred embodiment of the invention is the use of a photosensitive agent, or the precursor thereof, capable of producing ROS for the in vitro activation of stem cells, and another additional embodiment, for the in vitro production of proteins of the prolactin family 2, still more preferably proliferin-2.

In the present application "activation of stem cells" means the stimulation of the proliferation and/or of the functional differentiation programs of stem cells.

The stimulation of stem cells according to the present invention has a direct potential application in the area of the bioengineering for the acceleration of the growth of skin equivalents of epidermal or dermo-epidermal component (artificial skins) used in regenerative medicine and as substrates to test the biological feasibility of pharmacological and cosmetic compounds. So that a technological embodiment of the invention is the use of a photosensitive agent, or the precursor thereof, capable of producing ROS for the generation of dermo-epidermal or epidermal skin equivalents.

The therapeutic use of the invention can also be expressed as a method of treatment by PDT of a disease related to stem cells, preferably epidermal stem cells, in a subject preferably human, comprising administering to said subject affected by the disease a therapeutically effective amount of a photosensitive agent or the precursor thereof, capable of producing ROS. A preferred embodiment is a method of treatment by PDT of a disease related to stem cells, comprising administering a therapeutically effective amount of a pharmaceutical composition of a photosensitive agent or the precursor thereof, capable of producing ROS to a subject preferably human in need thereof. In this sense, the most preferred embodiment of the invention is a method of treatment by PDT of a disease related to epidermal stem cells in a human, comprising administering to said human affected by the disease a therapeutically effective amount of methyl aminolevulinate.

The therapeutic use of the invention can also be expressed as a photosensitive agent or the precursor thereof, capable of producing ROS for use in the treatment by PDT of a disease related to stem cells in a subject, preferably epidermal stem cells. Another embodiment is that they are hematopoietic stem cells.

Another additional embodiment of the invention is a photosensitive agent or the precursor thereof, capable of producing ROS and at least another therapeutic agent for use in the treatment by PDT of a disease related to stem cells in a subject, preferably epidermal stem cells.

Another preferred embodiment is the photosensitive agent of the invention, or the precursor thereof, capable of producing ROS for the in vitro activation of stem cells and another additional preferred embodiment is that it is for the in vitro production of proteins of the prolactin family 2, still more preferably proliferin-2.

In this sense, yet another additional embodiment is the photosensitive agent, or the precursor thereof, capable of producing ROS of the invention, for the generation of dermo-epidermal or epidermal skin equivalents.

The present invention relates to methods for functionally activating stem cells that can be applied to regenerative medicine for the treatment and recovery of skin wounds caused by burns, abrasions or other types of epithelial damage. The invention represents the ultimate technological advantage over the grafting techniques that allows the in situ stimulation of the stem cells of the hair follicle to contribute to epithelial regeneration without removing them from their own niche, thus eliminating all risk associated with external manipulation. The results of the examples provided (Example 8) indicate that PDT is capable of inducing the activation and mobilization of epidermal stem cells residing in the prominent region towards the hair bulb region, from where they promote hair growth.

Its application for the alternative treatment of ulcers, chronic wounds of small or medium size as well as for the treatment of skin diseases associated with a dysfunction or loss of epidermal stem cells is also proposed. Also its use as coadjuvant in cosmetic dermatology treatments after performing surgery on exposed and visible areas, and in patients undergoing cosmetic surgery procedures.

Other preferred embodiments of the invention are related to the cosmetic or pharmaceutical composition comprising a cosmetically or pharmaceutically effective amount of a photosensitive agent, or the precursor thereof, and at least one cosmetically or pharmaceutically acceptable excipient or adjuvant. In this sense, a preferred embodiment of the invention is that the photosensitive agent of said composition is protoporphyrin IX; or rather that the precursor of said photosensitive agent is 5-aminolevulinic acid or the chemical derivatives thereof, and among these chemical derivatives preferably methyl aminolevulinate (MAL).

Another preferred embodiment is that the photosensitive agent of the invention, or the precursor thereof, is incorporated into a cosmetically or pharmaceutically acceptable vehiculization system or into a sustained release system selected from the group consisting of liposomes, mixed liposomes, oleosomes, niosomes, ethosomes, millicapsules, microcapsules, nanocapsules, sponges, cyclodextrins, vesicles, micelles, surfactant mixed micelles, phospholipid-surfactant mixed micelles, millispheres, microspheres, nanospheres, lipospheres, microemulsions, nanoemulsions, miniparticles, milliparticles, microparticles, nanoparticles, lipid solid nanoparticles and nanostructured lipid carriers.

Another additional preferred embodiment is that the cosmetic or pharmaceutical composition of the invention is presented in a formulation selected from the group consisting of creams, multiple emulsions, anhydrous compositions, aqueous dispersions, oils, milks, balms, foams, lotions, gels, cream gels, hydroalcoholic solutions, hydroglycolic solutions, hydrogels, liniments, serums, soaps, shampoos, conditioners, serums, unguents, mousses, ointments, powders, bars, pencils, vaporizers, aerosols, capsules, gelatin capsules, soft capsules, hard capsules, tablets, sugar coated tablets, granulated forms, chewing gums, solutions, suspensions, emulsions, syrups, polysaccharides films, jellies and gelatin.

In another preferred embodiment, said composition is incorporated into a product selected from the group consisting of concealers, make-up foundations, cleansing lotions, cleansing milks, eye shadows, lipsticks, lip glosses, lip balms and powders.

In another additional embodiment, the photosensitive agent of the composition of the invention, or the precursor thereof, is incorporated into a fabric, non-woven-fabric or a medical product, preferably selected from the group consisting of bandages, gauze, shirts, tights, socks, underwear, girdles, gloves, diapers, sanitary napkins, dressings, bedspreads, towels, adhesive patches, non-adhesive patches, occlusive patches, microelectric-patches and face masks.

A preferred embodiment is that the adjuvant of the composition of the invention is selected from the group consisting of heat shock proteins, other stimulatory agents of the synthesis of the heat shock proteins, inhibitors of the aggregation of the acetylcholine receptors, inhibitors of muscle contraction, anticholinergic agents, elastase inhibitors, inhibitors of the matrix metalloproteinases, inhibitors or agents stimulating the synthesis of melanin, depigmenting or bleaching agents, propigmenting agents, self-tanning agents, anti-aging agents, inhibitors of the NO-synthase, inhibitors of the 5α-reductase, lysyl- and/or prolyl-hydroxylase inhibitors, antioxidants, free radical scavenging and/or anti air pollution agents, reactive carbonyl species scavenging agents, anti-glycation agents, antihistamines, antiviral agents, antiparasitic agents, emulsifiers, emollients, organic solvents, liquid propellants, skin conditioners, humectants, moisture retaining substances, alpha hydroxy acids, beta hydroxy acids, moisturizers, epidermal hydrolytic enzymes, vitamins, amino acids, proteins, pigments or colorants, dyes, gelling polymers, thickeners, surfactants, softeners, anti-wrinkle agents, agents capable of reducing or treating the bags under the eyes, exfoliating agents, antimicrobial agents, antifungal agents, fungistatic agents, bactericidal agents, bacteriostatic agents, agents stimulating the synthesis of dermal or epidermal macromolecules and/or able to inhibit or prevent their degradation, agents stimulating the synthesis of collagen, agents stimulating the synthesis of elastin, agents stimulating the synthesis of decorin, agents stimulating the synthesis of laminin, agents stimulating the synthesis of defensins, agents stimulating the synthesis of aquaporins, agents stimulating the synthesis of hyaluronic acid, agents stimulating the synthesis of fibronectin, agents stimulating the synthesis of sirtuins, agents stimulating the synthesis of lipids and components of the stratum corneum, ceramides, fatty acids, inhibitors of the degradation of collagen, inhibitors of the degradation of elastin, inhibitors of serine proteases such as cathepsin G, agents stimulating the proliferation of fibroblasts, agents stimulating the proliferation of keratinocytes, agents stimulating the proliferation of adipocytes, agents stimulating the proliferation of melanocytes, agents stimulating the differentiation of keratinocytes, agents stimulating the differentiation of adipocytes, inhibitors of the acetylcholinesterase, skin relaxing agents, agents stimulating the synthesis of glycosaminoglycans, anti hyperkeratosis agents, comedolytic agents, antipsoriasis agents, DNA repairing agents, DNA protecting agents, stabilizers, antipruritic agents, agents for the treatment and/or care of sensitive skin, firming agents, anti-stretch mark agents, astringent agents, agents regulating sebum production, lipolytic agents or agents stimulating lipolysis, anti-cellulite agents, anti-perspirant agents, agents stimulating wound healing, wound healing coadjuvant agents, agents stimulating the reepithelialization, reepithelialization coadjuvant agents, cytokine growth factors, soothing agents, anti-inflammatory and/or analgesic agents, anesthetic agents, agents acting on capillary circulation and/or microcirculation, agents stimulating the angiogenesis, inhibitors of the vascular permeability, venotonic agents, agents acting on the metabolism of the cells, agents intended to improve the dermal-epidermal junction, agents inducing hair growth, agents inhibiting or retarding hair growth, agents delaying hair loss, preservatives, perfumes, chelating agents, plant extracts, essential oils, marine extracts, agents coming from a biofermentation process, mineral salts, cell extracts, sunscreens and photoprotective agents of mineral or organic nature active against ultraviolet rays A and/or B, or mixtures thereof.

Said anti-wrinkle agents and/or anti-aging agents are selected from the group consisting of Acetyl Hexapeptide-8, Acetyl Heptapeptide-4, Acetyl Octapeptide-3, Pentapeptide-18, Acetyl Hexapeptide-25, Diaminopropionoyl tripeptide-33, Tripeptide-10 Citrulline, Acetyl Tetrapeptide-5, Acetyl Tripeptide-30 Citrulline, Acetyl Tetrapeptide-30, Dimethylmethoxy chromanol, Dimethylmethoxy Chromanyl palmitate, *pseudoalteromonas* ferment extract, Ca2+ channel antagonists, retinol and its derivatives, idebenone and its derivatives, Coenzyme Q10 and its derivatives, boswellic acid and its derivatives, GHK and its derivatives and/or salts, carnosine and its derivatives, DNA repair enzymes, chloride channel agonists, the mixture of Hydrolyzed Wheat Protein, Hydrolyzed Soy Protein and Tripeptide-1, the mixture of Lysine HCl, Lecithin and Tripeptide-10 Citrulline and the mixture of *Pseudoalteromonas* ferment extract, Hydrolyzed Wheat Protein, Hydrolyzed Soy Protein, Tripeptide-10 Citrulline and Tripeptide-1.

In another preferred embodiment said agent stimulating wound healing and/or reepithelialization or wound healing and/or reepithelialization coadjuvant agent is selected from the group consisting of *Pseudoalteromonas* ferment extract and Tripeptide-10 Citrulline.

In another additional preferred embodiment, said adjuvant is of synthetic origin or is a plant extract or is derived from a biotechnological process or is derived from a combination of a synthetic procedure and a biotechnological process.

The labeled cells generated (Label Retaining Cells, LRCs) were detected by administering serial injections of the thymidine analogue BrdU to neonatal mice and further analysis at 50 days, and quantification by immunofluorescence in "in toto" mounts of epidermis of the tail of adult mice. A significant increase in LRCs was observed in the prominent region of the hair follicle (HF) in telogen two days after treatment (PDT 2d) with respect to the controls, indicating stimulation of the proliferation of the epidermal stem cells of the HF in response to treatment. The bars indicate the standard error. Scale bar: 100 μm. ***: significant, P<0.001.

Figure 2:
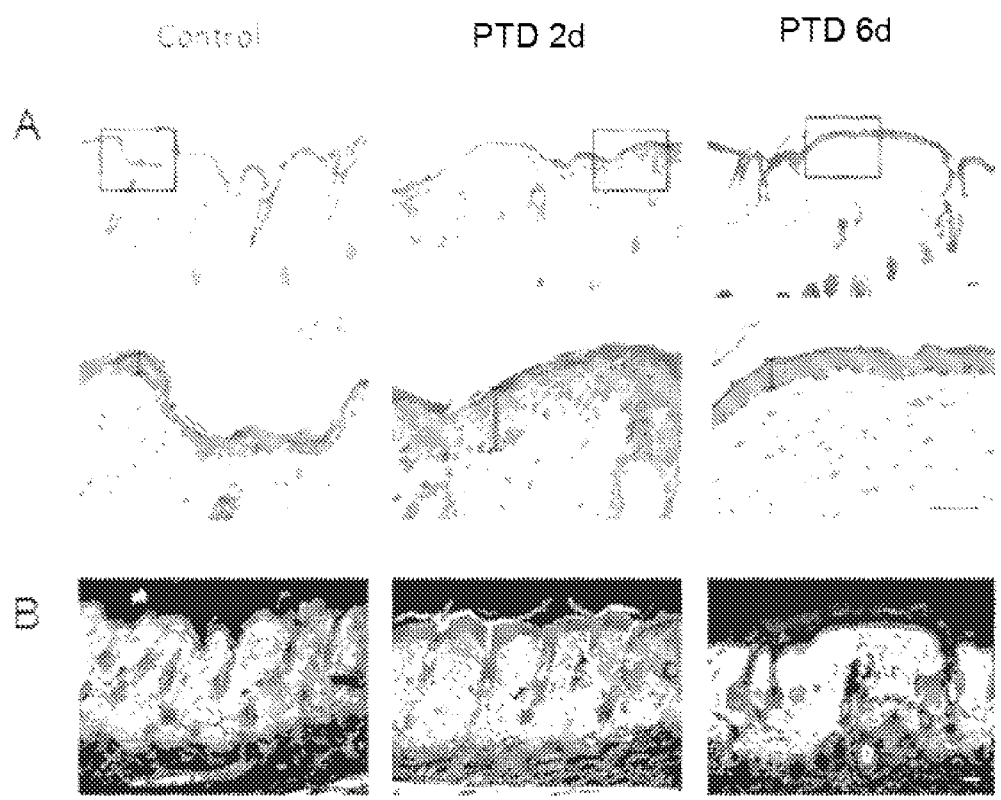

FIG. 2. The PDT induces transient morphological changes in the skin.

A: In the histological sections of dorsal skin of the back a transient hyperplasia was observed in the epidermis two days after the photodynamic stimulation, which reverted six days after the same. The areas highlighted in the upper panels are shown in detail in the lower panels.

B: The fluorescence of the eosin revealed an increase in the density of collagen fibers of the dermis observed 6 days after the PDT. Staining: H-E. Scale bar: 20 μm.

Figure 3:
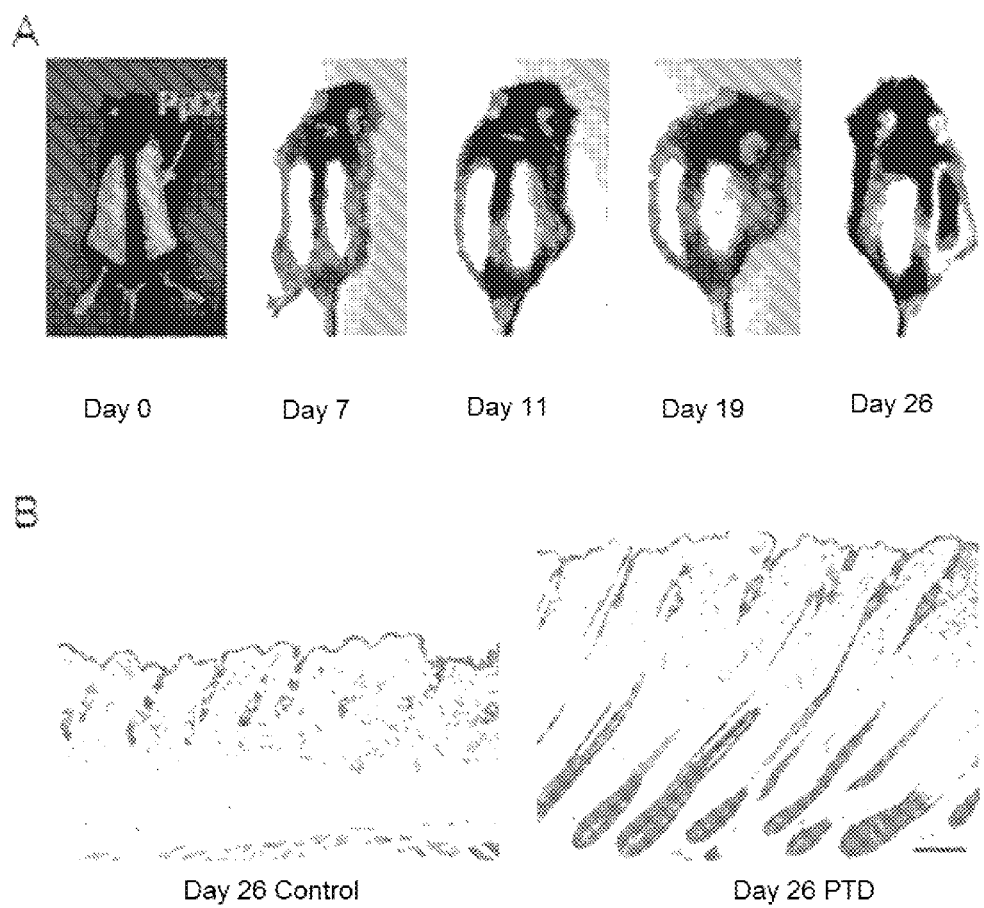

FIG. 3. The PDT induces hair growth.

A: Two separate areas of the skin of the dorsum of the mice were shaved and Metvix® was applied topically on the right region, while the left, used as a control, was left without treatment. The PpIX production in the region treated with Metvix® (Day 0) was checked by red fluorescence emission under excitation with ultraviolet light. After the PDT, accelerated hair growth was observed in the treated skin region with respect to the control (Day 7 to 26).

B: The histological sections stained with H-E of samples from dorsal skin obtained 26 days after the treatment showed the progress of the anagen phase of the HFs in the skin treated with PDT. Scale bar: 100 μm.

Figure 4:
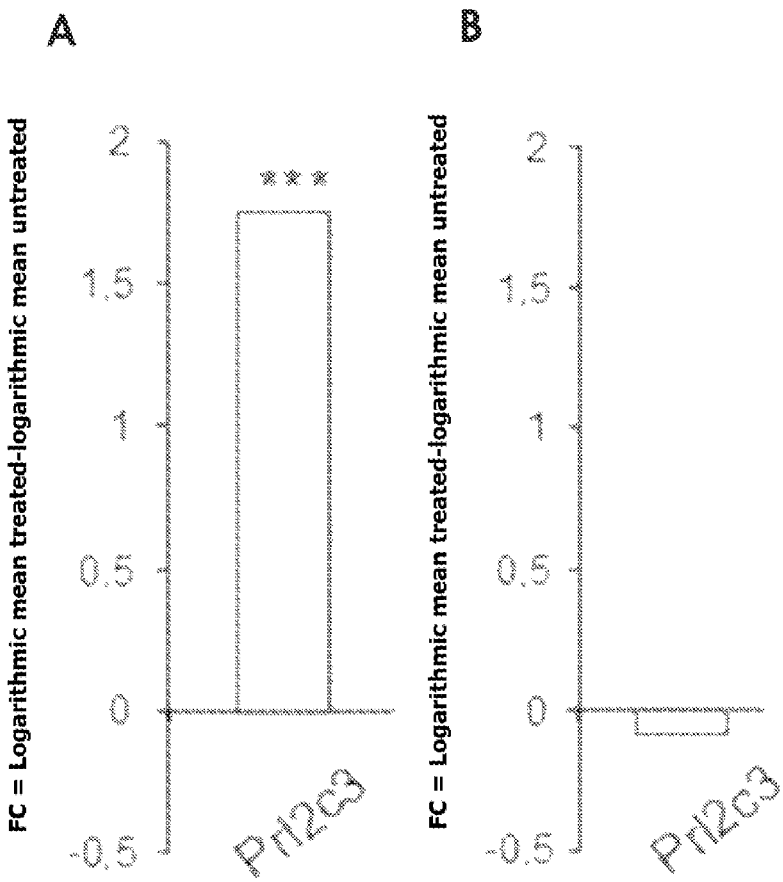

FIG. 4. The PDT causes changes in the gene expression of the skin.

A: The analysis by quantitative real-time PCR from samples of skin of the backs of mice treated and their corresponding controls showed the induction of the mRNA of Pr12c3, encoding proliferin-2, two days after application of PDT-MAL.

B: Six days after the treatment, no significant changes were observed in the expression of the Pr12c3 mRNA. 18S ribosomal RNA was used as endogenous for the normalization and the relative quantification (RQ) was calculated based on the control. ***: significant, P<0.001.

Figure 5:
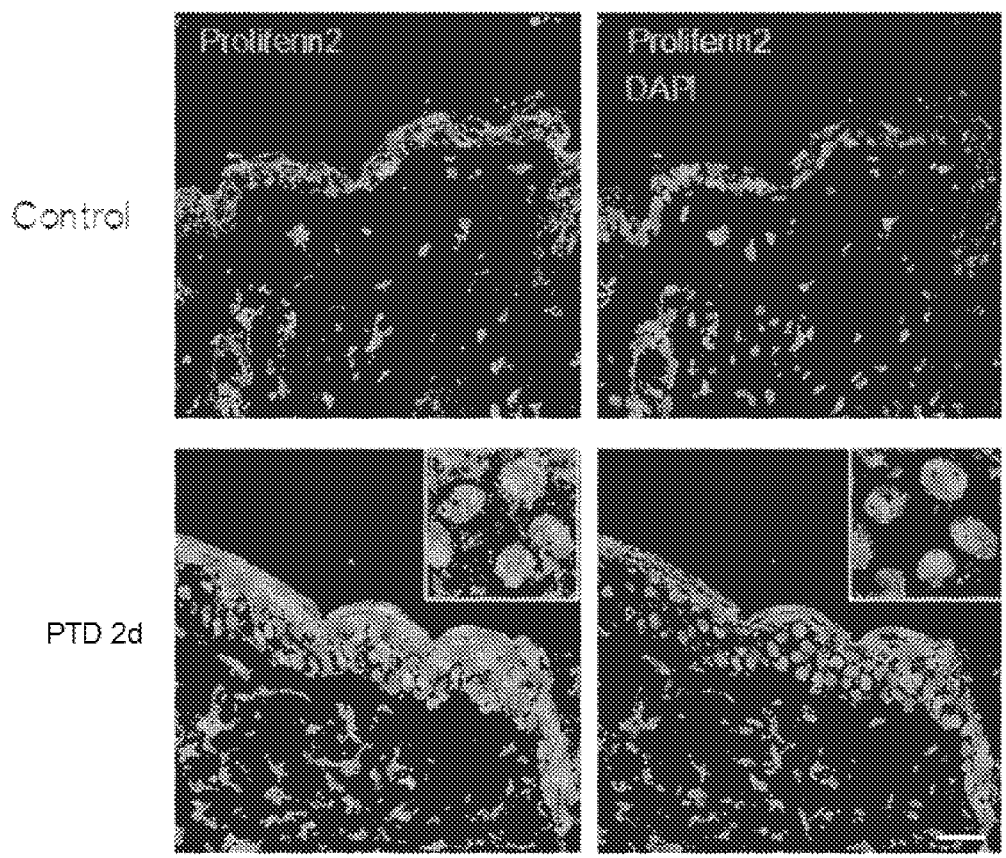

FIG. 5. The PDT causes changes in the expression and localization of proliferin-2 in the skin. The immunofluorescence in histological sections of skin showed an increase in proliferin-2 expression in the epidermis after the application of PDT-MAL and a novel nuclear localization of this protein as a result of the treatment. Scale bar: 50 μm.

Figure 6:
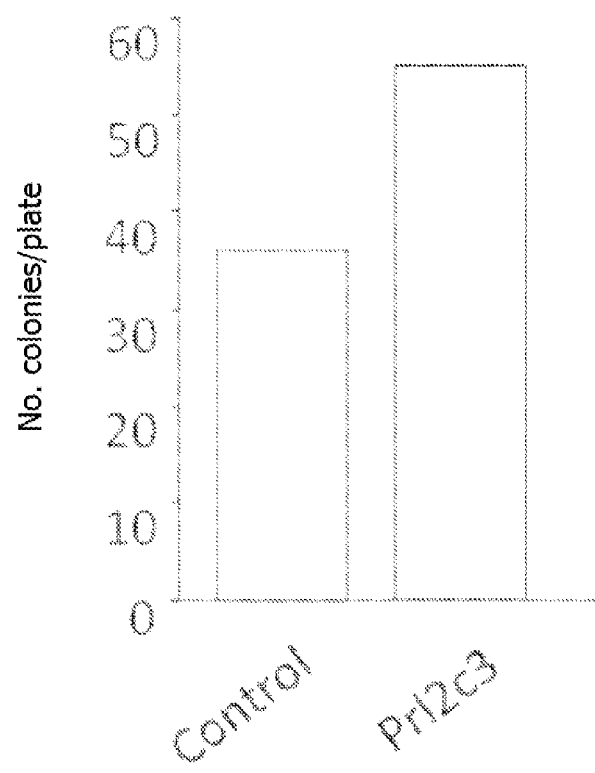

FIG. 6. Induction of in vitro growth and expansion of epidermal stem cells by Pr1c3. Epidermal stem cells were isolated from mouse skin and were grown in conditioned culture medium containing high amounts of Pr12c3 or in control medium. The number of colonies with a minimum of four cells, an indicator of sustained proliferative activity, was measured in these cultures within seven days. The results indicated significant increase in the number of colonies in the cultures of epidermal stem cells treated with growth medium conditioned by Pr12c3.

MODES OF PREFERRED EMBODIMENT

With the intention of showing the present invention in an illustrative manner but in no way limiting, the following examples are provided.

Example 1

Experimental Animals

Neonatal mice, ten days of age, of the C57BL/6 line were used for the labeling experiments of epidermal stem cells, and adults, 7 weeks of age, for the rest of tests. The animals used in each experiment were littermates and the comparisons were made between individuals of the same sex, to avoid differences attributable to this factor. The experiments were carried out pursuant to the regulations governing the handling and care of laboratory animals (Royal Decree 1201/2005).

Example 2

Application of the Photodynamic Therapy

The skin of the back of the mice was shaved and depilatory cream was applied (Veet®). The next day, the methylated derivative of ALA (MAL) was administered on the skin of the back and the tail as a commercial cream (Metvix®, Galderma) and incubated in the dark for 5 hours, after which the excess Metvix® was removed by washing with PBS. The endogenous production of PpIX in the skin of the back was checked by the emission of red fluorescence characteristic of PpIX under excitation with ultraviolet light (UV) of 407 nm, using a digital camera provided with two lamps of said wavelength. Next, the animals were anesthetized by intraperitoneal injection (i.p.) of a solution 3:1 of Imalgene 500 (Merial) and Domtor (Pfizer) (50 µl/mouse; 0.864 mg of ketamine hydrochloride and 0.005 mg of medetomidine hydrochloride per 10 g of body weight). The irradiation with red light at 636 nm was carried out evenly over the dorsal surface of the tail and the back for 3.5 minutes, using a diode lamp of 36 J/cm2 (Aktilite®) located about 5 cm from the animal. After the exposure to red light, the animals received a subcutaneous injection of Antisedan (Pfizer) 2:1 with respect to the volume of Domtor administered, and were kept on thermal blankets until complete recovery. After the time determined by each test passed, the animals were sacrificed in $CO_2$ chamber and the skin was processed for the different analyses.

In the case of functional experiments of capillary induction, the skin of the back was previously shaved in two separate areas and Metvix® was applied only on the right region, keeping the left half as a control.

Example 3

Labeling of Epidermal Stem Cells Identified as "Label Retaining Cells" (LRCs)

The epidermal stem cells were labeled and identified according to the Braun protocol (Braun et al, "Manipulation of stem cell proliferation and lineage commitment: visualisation of label-retaining cells in wholemounts of mouse epidermis". Development. 130: 5241-55, 2003). The neonatal mice received an i.p. injection of 50 mg/Kg body weight BrdU (Sigma-Aldrich) (80 µl BrdU 6.25 mg/ml) in PBS once a day for four consecutive days, with the purpose of extensively labeling the DNA in all the cells of the skin. After 7 weeks, the epidermal stem cells were identified based on the low replication rate that characterizes them as those cells capable of retaining the BrdU label ("Label Retaining Cells", LRCs) for an extended period of time due to the sporadic replication of their DNA. The identification and quantification of LRCs after PDT-MAL treatment was carried out by immunofluorescence in in toto mounts of the tail epidermis that were observed in a confocal microscope.

Example 4

Processing of the Skin, Histology and Immunofluorescence

Immediately after sacrificing the animal, the tail was separated from the body and a scalpel incision was made in the ventral area of the same, the skin being excised manually in one single piece. This was incubated in 10 ml of 5 mM EDTA in PBS for 6 hours at 37° C. and, next, the epidermis was separated from the dermis with the help of clamps. The samples of epidermis were transversely divided into two portions: one was frozen at −80° C. for RNA extraction and the other was fixed in 3.7% formaldehyde in PBS for 48 hrs at 4° C., washed in PBS and stored in 0.02% PBS-sodium azide for the preparation of in toto mounts.

On the other hand, the skin of the back was extracted and fixed in 3.7% formaldehyde in PBS for at least 48 hrs at 4° C. Next, they were embedded in paraffin following the usual protocols and 4 µm histological sections were prepared that were stained with hematoxylin-eosin (HE) or processed for immunofluorescence (IF), using in the latter case slides treated with poly L-lysine. For the IF tests, the deparaffinized and hydrated sections were permeabilized in 0.1% Triton X-100 in PBS, the autofluorescence was removed by incubation with 50 mM NH4CI (10 min at room temperature) and were blocked in 0.3% bovine serum albumin (BSA, Sigma) in PBS (1 hr at room temperature). The blocked samples were incubated overnight at 4° C. with polyclonal antibody (Santa Cruz Biotechnology) against proteins of the prolactin family 2 (proliferins), including proliferin-2 (Pr12c3). Then they were washed in PBS and incubated with the corresponding Cy3-coupled secondary antibody (Jackson ImmunoResearch Laboratories). Finally, the samples were washed in PBS and mounted with Vectashield (Vector Labs) containing 5 ng/ml of DAPI (Merck). For the detection of LRCs by immunofluorescence in in toto mounts, the epidermis pieces of the tail were incubated with 1 N HCl (45 min at 37° C.) and Tris-borate-EDTA (5 min at room temperature), performing two brief washes with distilled water after each incubation. They were then permeabilized and blocked in PTG buffer (0.5% Triton X-100, 0.2% gelatin in PBS) for 1 hr at room temperature, after which they were incubated with the monoclonal mouse primary antibody anti-BrdU conjugated with fluorescein isothiocyanate (FITC) (Roche), overnight at 37° C. Next, they were repeatedly washed in PBS and mounted with Vectashield-DAPI. The immunofluorescence samples were analyzed in a spectral confocal microscope Leica TCS-SP2-AOBS using 488 nm excitation lasers for FITC, 633 nm for Cy3 and UV for DAPI. The three-dimensional reconstructions were carried out with the help of the software LCS Suite version 2.61 (Leica) and were then processed with the software Photoshop CS3 Extended version 10.0.1 (Adobe). The histological sections stained with HE were analyzed on an Olympus BX61 fluorescence microscope coupled to a digital capture camera Olympus DP50, using clear field and blue excitation light (excitation filter BP 460-490 and barrier filter BA 520IF).

Example 5

Pr12c3 RNA Extraction, Analysis of Large-Scale Patterns of Gene Expression and qRT-PCR The RNA purification of Pr12c3 from the epidermis of the tail and the skin of the back was carried out by organic extraction with TriPure™ Isolation Reagent (Roche) followed by a column purification (RNeasy Mini kit, QIAGEN). The tissue was disintegrated with scissors and homogenized in TriPure with a polytron (PT 1200 E, Kinematica). The homogenate was phase separated in chloroform: isoamyl (Merck) and the RNA of the aqueous phase was purified by column. The concentration and purity of the RNA (ratio A260:A280>1.8) were determined by spectrophotometry (Nanodrop ND1000, Nanodrop Technologies). The large scale gene expression analysis was carried out by arrays from Agilent Technologies (Agilent. SingleColor. 14868). The expression analysis by real-time quantitative PCR (qRT-PCR) was carried out using the system from Applied Biosystems 7900HT Fast Real Time PCR with SYBR Green.

Results

Example 6

Figure 1:
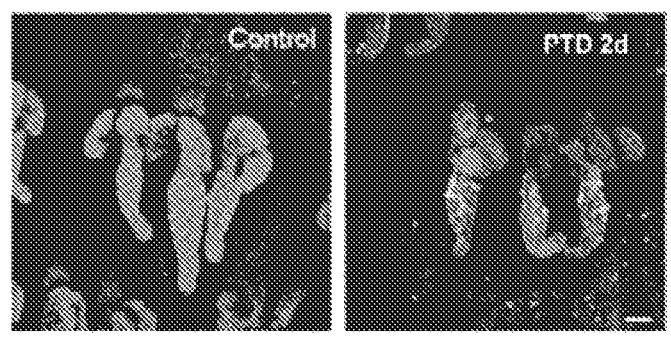
FIG. 1. The PDT induces cell proliferation in the prominent region of the hair follicle.
Figure 1:
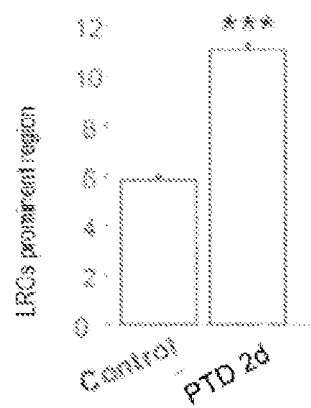

Induction of Proliferation of the Stem Cells Resident in the Prominent Region of the Hair Follicle by the PDT-MAL Treatment In order to analyze the effect of the PDT-MAL treatment on the activity of the epidermal stem cells, the hair follicle (HF) was used as model, the prominent region of which is the main reservoir of stem cells of the skin. The stem cells were identified because of their characteristic low proliferation rate, which allows the retention of a BrdU nuclear label for an extended period of time after the serial administration of the nucleotide analog in the neonatal age, allowing identifying them as LRCs (Braun et al, "Manipulation of stem cell proliferation and lineage commitment: visualisation of label-retaining cells in wholemounts of mouse epidermis". Development. 130: 5241-55, 2003; Cotsarelis et al, "Label-retaining cells reside in the bulge area of pilosebaceous unit: implications for follicular stem cells, hair cycle, and skin carcinogenesis". Cell 61, 1329-37, 1990). As shown in FIG. 1, the immunofluorescence analysis in in toto mounts of epidermis of the tail of control mice and undergoing PDT-MAL showed a significant increase (P<0.001) of the number of LRCs in the prominent region of the HFs.

Example 7

Induction of Transient Hyperplasia in the Epidermis and Increase in the Density of Collagen Fibers in the Dermis by the PDT-MAL Treatment The large-scale morphological changes produced by PDT-MAL were characterized in histological sections of dorsal skin of the back stained with HE. The analysis of these sections indicated that the treatment induced a transient hyperplasia in the epidermis, showing the most apparent response 2 days after the treatment and reverting to a normal state 7 days after the same (FIG. 2A). Very marked changes were also observed in the morphology of the dermis, which had a sharp increase in the density of collagen fibers 7 days after MAL-PDT treatment, characterized as an increase in the specific fluorescence emission of the eosin interspersed in the collagen fibers (Espada et al. "Selective fluorescence of eosinophilic structures in grasshopper and mammalian testis stained with haematoxylin-eosin" Histochemistry 99: 385-390, 1993) (FIG. 2B).

Example 8

Acceleration of Hair Growth by PDT-MAL Treatment

With the purpose of analyzing the dynamics of hair growth in the skin undergoing PDT-MAL, we proceeded to shave the skin of the back of the mice and Metvix® was applied topically on the right dorsal region, keeping the left as a control, as detailed in Example 2. After 5 hours of incubation in the dark, PpIX production was determined by analysis of the red fluorescent emission characteristic of this compound. The results obtained showed that the production of PpIX from MAL in the epidermis took place in the presence of Metvix®, as indicated by the fluorescent signal observed under UV excitation light (FIG. 3A, day 0). Next, the PDT was completed by radiating the back of the mice with a red light. The developments in the subsequent days showed noticeably accelerated hair growth in the half treated with respect to the control skin (FIG. 3A, 7 to 26 days). The histological sections corresponding to skin samples taken 26 days after the PDT show the development achieved by the HFs (FIG. 3b). Thus while the HFs in the control skin remain at rest (telogen) and in no case exceed the dermis, the progress of the growth phase (anagen) is observed in the treated skin and the region of the hair bulb largely penetrates into the layer underlying the dermis.

Example 9

Specific Induction of the Pr12c3 Gene by PDT-MAL Treatment

To determine the changes in the gene expression pattern induced in the skin by the MAL PDT-treatment, a large scale analysis was carried out in RNA micro-arrays using mRNA obtained from the skin of the back and the epidermis of the tail. By this approach the product of the Pr12c3 gene was identified as the mRNA, the expression of which was most strongly modified in response to the PDT-MAL treatment, which result was validated by qRT-PCR (FIG. 4). The immunolocalization of the protein Pr12c3 in histological sections of dorsal skin showed a low intensity and diffuse pattern in cytoplasm in the epidermis of the control animals, while the increase in the expression levels after treatment was confirmed, revealing a novel nuclear localization of this protein in the animals undergoing PDT-MAL (FIG. 5).

Example 10

Induction of the In Vitro Growth and Expansion of Epidermal Stem Cells by a Culture Medium Containing High Amounts of Pr12c3

First, it was proceeded to the isolation of the Pr12c3 cDNA by RT-PCR and subsequent cloning in the expression vector pcDNA3.1A and transfection of this vector in HEK293T cells. By means of immunoblotting it was confirmed that the culture medium conditioned by the growth of cells transfected with the cloned vector contained an average of up to 10 times more protein Pr1c3 than a control medium of cells transfected with the empty vector. Subsequently, epidermal stem cells were isolated from mouse skin in accordance with protocols established (Espada et al. "Nuclear envelope defects cause stem cell dysfuction in premature-aging mice" J. Cell Biol. 181: 27, 35, 2008). These cultures were treated with conditioned medium. The cultures with conditioned medium showed a significantly higher number of colonies with more than 4 cells than the control cultures treated with medium from cells transfected with the empty vector (FIG. 6).

The invention claimed is:

1. An in vitro method for producing artificial skin or skin equivalents by activation of skin stem cells comprising:
   isolating skin stem cells;
   preparing a culture including the isolated skin stem cells;
   exposing the culture to protoporphyrin IX, or a precursor thereof, capable of producing reactive oxygen species to obtain a product thereof;
   exposing the product thereof to red light, thereby obtaining stimulated, proliferated and/or functionally differentiated skin stem cells; and
   producing artificial skin or skin equivalents from the stimulated, proliferated and/or functionally differentiated skin stem cells.

2. The method of claim 1, wherein the product obtained by exposing the culture to protoporphyrin IX, or the precursor thereof, capable of producing reactive oxygen species, comprises proteins of the prolactin family 2.

3. The method according to claim 2, wherein said protein of the prolactin family 2 is proliferin-2.

* * * * *